United States Patent [19]
Christoudias

[11] Patent Number: 5,403,332
[45] Date of Patent: Apr. 4, 1995

[54] MARITSA TISSUE APPROXIMATOR AND METHOD OF USING THE SAME

[76] Inventor: George C. Christoudias, 17 Lower Cross Rd., Saddle River, N.J. 07458

[21] Appl. No.: 205,389

[22] Filed: Mar. 4, 1994

Related U.S. Application Data

[63] Continuation of Ser. No. 151,795, Nov. 15, 1993.

[51] Int. Cl.⁶ ............................................. A61B 17/28
[52] U.S. Cl. ................................. 606/148; 606/205; 606/206; 606/207; 606/150; 294/19.1; 294/115; 294/87.1
[58] Field of Search ............... 606/205, 206, 208, 150, 606/207, 148; 81/308, 309; 433/154, 155, 159; 294/19.1, 115, 87.1

[56] References Cited

U.S. PATENT DOCUMENTS

| | | | |
|---|---|---|---|
| 677,577 | 7/1901 | Lancaster | 606/205 X |
| 848,126 | 3/1907 | Roosevelt | 606/205 X |
| 1,413,896 | 4/1922 | Brix | 606/205 X |
| 2,214,985 | 9/1940 | Bachmann | 606/208 X |
| 5,209,747 | 5/1993 | Knoepfler | 606/208 X |
| 5,228,451 | 7/1993 | Bales et al. | 606/205 X |
| 5,281,230 | 1/1994 | Heidmueller | 606/205 X |

Primary Examiner—Michael H. Thaler
Attorney, Agent, or Firm—Richard A. Joel

[57] ABSTRACT

This invention comprises an instrument for peritoneal approximation following the application of mesh in a laparoscopic herniorrhaphy or for approximating any tissues that could physically reach each other during the performance of any laparoscopic procedure. The Maritsa Tissue Approximator comprises an elongated cylinder which is divided into two elongated compartments by a central plate which extends outwardly from the bottom of the cylinder. The head of the instrument comprises the outwardly extending fixed plate and two independently controlled jaws which close separately over the fixed central plate. The jaws are pivotally mounted onto a lateral extension of the center plate by pin-means about which they rotate thus opening or closing over the fixed central plate. The rotation about the pin is caused by a control wire which extends through a compartment of the cylinder and is affixed to a pivotal member at the other end of the instrument. The two jaws are each controlled by operation of a separate pivotal member which is resiliently backed against the handle and moved in conjunction with the pressure applied thereto, thus opening or closing the jaws on the opposite end of the instrument to expeditiously move a tissue flap into approximation with the opposite flap to facilitate stapling of the incision.

9 Claims, 4 Drawing Sheets

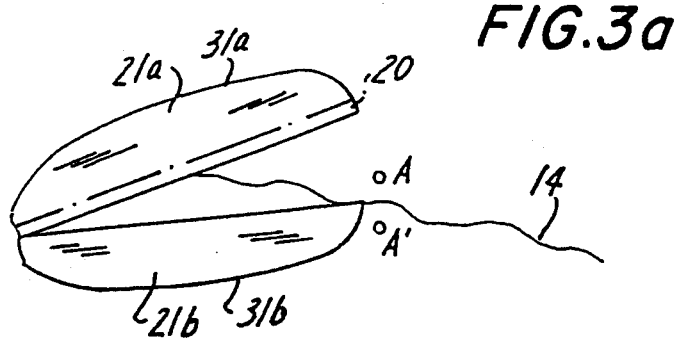
FIG.3a
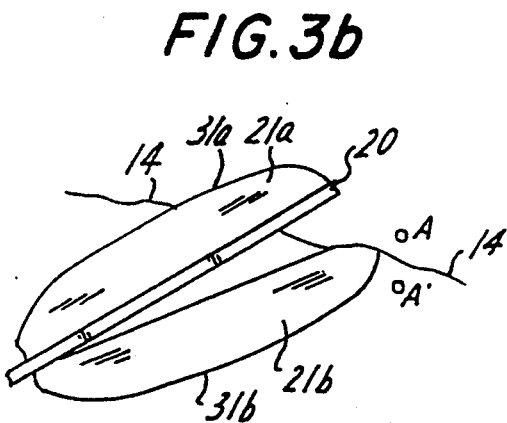
FIG.3b
FIG.3c
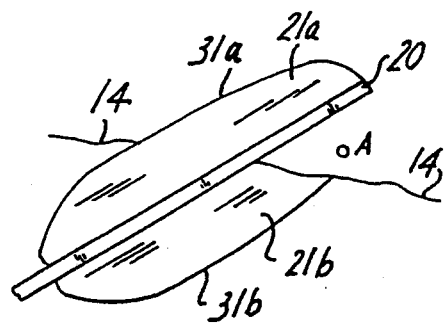
FIG.3d
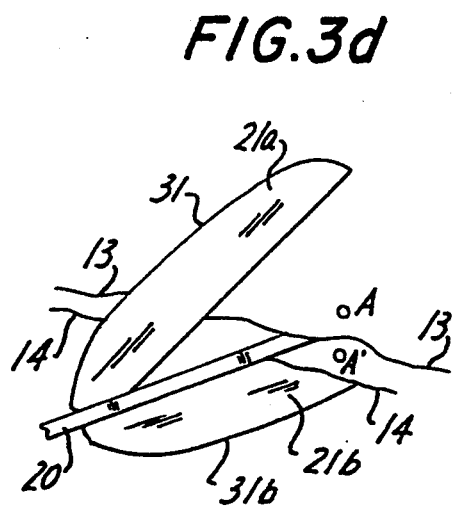
FIG.3e
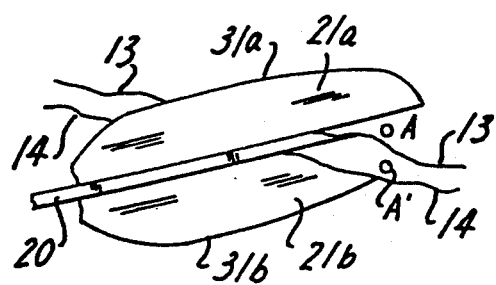

MARITSA TISSUE APPROXIMATOR AND METHOD OF USING THE SAME

This is a continuation of Ser. No. 08/151,795, filed Nov. 15, 1993.

BACKGROUND OF THE INVENTION

In the performance of a laparoscopic herniorrhaphy, a linear incision is made on a peritoneum from a first point to a second point. Proximal and distal peritoneal flaps are then developed. The hernia repair is done and to complete the laparoscopic part of the procedure, the proximal and distal peritoneal flaps have to be approximated. The present invention permits this approximation to be done readily and efficiently.

In the prior art, where the proximal and distal peritoneal flaps have to be approximated, the more mobile distal flap is generally held with a grasper and pulled to a corresponding point on the less mobile proximal flap. A staple gun is then used to staple a fixed point on the distal end held by the grasper to a loose point on the proximal flap. This procedure is cumbersome and can be time consuming. It is not unusual for the loose point of the proximal flap to be pushed away by the stapler before the staple is fired and miss it altogether or hold a minimal amount of tissue at a point on the proximal peritoneal flap.

The present invention permits approximating any tissues that can physically reach each other during the performance of a laaroscopic procedure. With the flaps held together by the present invention, the suturing or stapling of the flaps is greatly facilitated. An approximator with two independent jaws is used to grasp both flaps against a central protruding plate and hold the tissue for stapling or suturing.

SUMMARY OF THE INVENTION

This invention, known as the Maritsa Tissue Approximator, relates to laparoscopic surgery and in particular to an apparatus and method employed in laparoscopic herniorrhaphy, wherein the laparoscopic tissue is approximated by the apparatus. The Maritsa Tissue Approximator comprises a cylinder having a central diametrical plate dividing the cylinder into two compartments. The control end of the approximator includes a handle and two independently operated triggers with a control wire coupled to each trigger. The head of the approximator includes a pair of independently operated jaws that close over the protruding central plate. The pivotal jaws are each connected by a control wire to one of the triggers. This allows each jaw to open and close independently of each other over the fixed plate.

In operation, the separated edges of a tissue can be approximated one at a time bringing them together in preparation for suturing and/or stapling them to each other. Specifically, a distal peritoneal flap is engaged between a first jaw and the fixed plate by closing the jaw over the fixed plate with the tissue therebetween. The head of the instrument is then moved to the proximal flap with the jaw closed, the second jaw is then opened and grasps the proximal flap, thus approximating and holding the two flaps together for suturing or stapling. The held tissue may be moved to the left held tissue may be moved to the left or the right pulling the proximal and distal flaps together for stapling with ease.

Accordingly, it is an object of this invention to provide a new and improved apparatus for approximating tissue in laparoscopic surgery.

An other object of this invention is to provide a new and improved approximator for approximating tissue in laparscopic surgery so that the tissue may be readily and expeditiously sutured or stapled after an operation.

A further object of this invention is to provide a new and improved approximator which includes independently operated jaws Which grasp the tissue flaps against a central plate to approximate them for suturing or stapling.

A more specific object of this invention is to provide a new and improved instrument for peritoneal approximation for following the application of mesh in a laparscopic herniorrhaphy which comprises an instrument, which is able to grasp the proximal and distal flaps of tissue and hold them together to facilitate suturing or stapling.

DESCRIPTION OF THE DRAWINGS

Other objects and advantages of this invention may be more clearly seen when viewed in conjunction with the accompanying drawings wherein

FIG. 2a shows the initial incision; FIG. 2b shows the distal flap away from the proximal flap, and FIG. 2c shows the approximator in action;

FIGS. 3a-e, shows the operation of the jaws in approximating the tissue;

DETAILED DESCRIPTION OF THE INVENTION

Figure 2A:
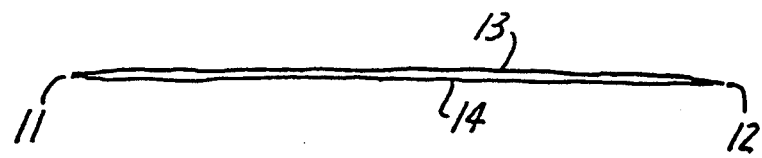
FIGS. 2a-c, show the tissue which is to be approximated by the invention at various stages.
Figure 2B:
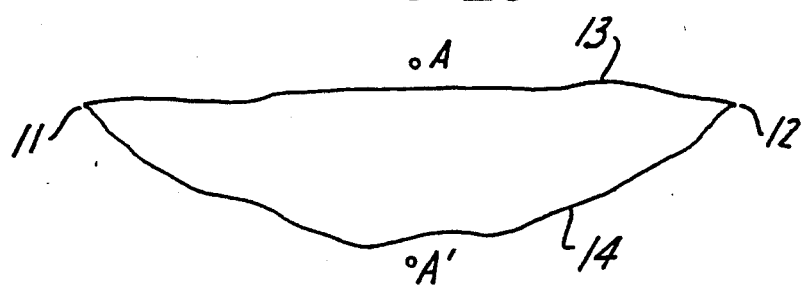
Figure 2C:
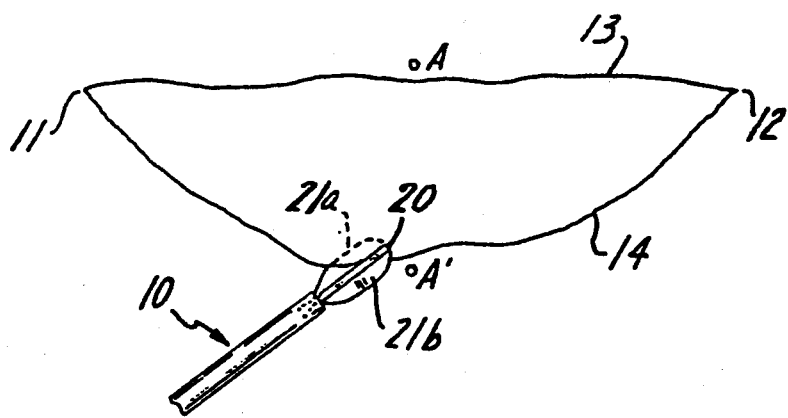

Referring now to the drawings the Maritsa Laparoscopic Tissue Approximator 10 is used particularly in laparoscopic herniorrhaphies, wherein a linear incision FIG. 2a, is made on peritoneum tissue from point 11 to point 12. Proximal 13 and distal 14 flaps are then developed, see FIG. 2b. After the hernia repair is accomplished and to complete the laparoscopic part of the procedure following the application of mesh (not shown), the proximal and distal peritoneal flaps 13 and 14 have to be approximated. This is accomplished by using the unique approximator 10 to grasp the distal flap 14, as shown in FIG. 2c and bring the flaps 13 and 14 together to facilitate suturing or stapling, see FIGS. 4a-c. FIGS. 3a to 3e show in greater detail the grasping of the flaps 13 and 14 by the approximator 10.

Figure 1:
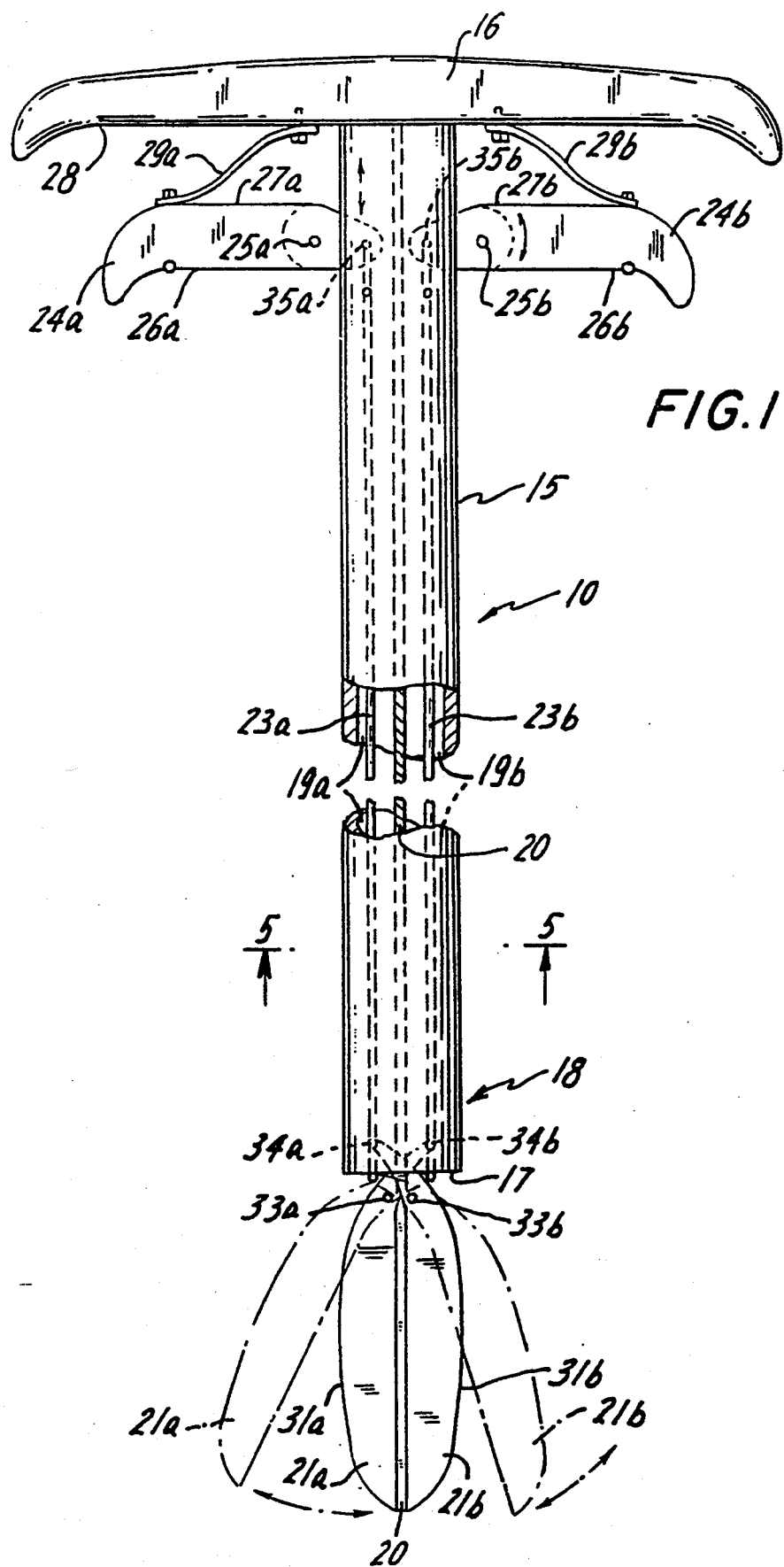
FIG. 1 is a front view of the invention with portions cutaway and the operation of the jaws shown in phantom.

The Maritsa Laparoscopic Tissue Approximator 10 is shown in FIG. 1 and includes an elongated cylinder 15 having a handle 16, at one end and an aperture 17, at the other end or head 18. The hollow cylinder 15, is divided into two compartments 19a and 19b, by a central plate 20, which extends diametrically across the cylinder and outwardly from the base aperture 17 for a predetermined distance. A pair of jaws 21a and b are mounted to the cylinder 15 and coupled at their upper ends 22a and b, to control wires 23a and b respectively, which extend through the compartments 19a and b in the cylinder to reach the respective triggers 24a and b. The triggers 24a and b are each pivotally mounted to the cylinder 15 at pins 25a and b respectively and extend outwardly with a downwardly curving lower surface 26a and b. The upper surface 27a and b of the triggers 24a and b is resiliently mounted against the lower surface 28 of the handle 16 by the leaf springs 29a and b.

The jaws 21a, 21b each comprise a curved outer surface 31a, 31b and a flat inner surface 32a, 32b. The jaws 21a, 21b pivot about pins 33a, 33b respectively when the corresponding trigger 24a or 24b is pressed. The triggers 24a and 24b are pivotally connected to the cylinder 15 by pins 25a and 25b and to control wires 23a and 23b by pins 35a and 35b respectively. The jaws 21a and 21b operate independently as the corresponding trigger 24a or 24b is pressed to engage or disengage with the protruding central plate 20 in the manner indicated by the arrows. The jaws 21a, 21b are connecting to the control wires 23a, 23b by pins 34a, 34b.

Figure 4A:
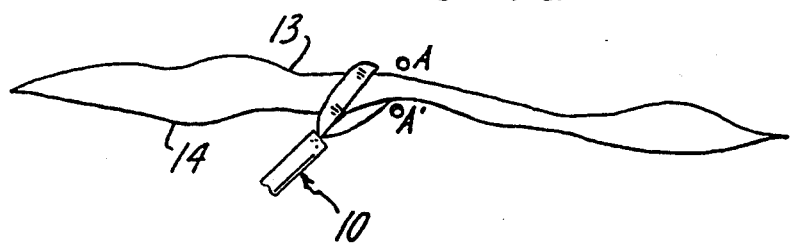
FIGS. 4a-c, shows the suturing or stapling of the tissue with the Maritsa Approximator being used.
Figure 4B:
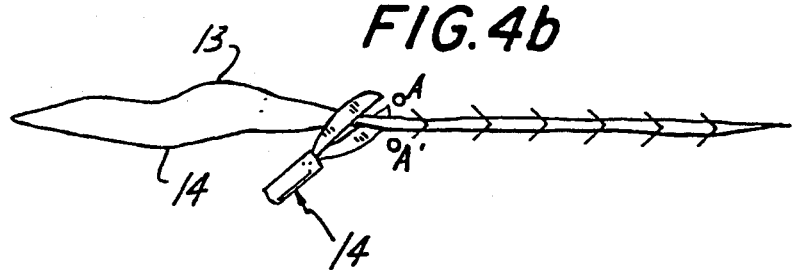
Figure 4C:
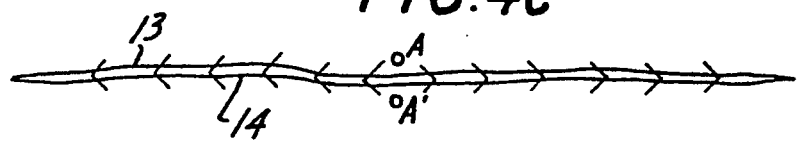

FIG. 2a discloses an incision from point 11 to point 12 exposing the tissue flaps 13 and 14. FIG. 2b depicts the distal flap moved backwardly from the incision. Point A' of the distal flap 14 is engaged by the Maritsa Tissue Approximator and moved towards point A the proximal flap 13. To accomplish this operation the trigger 24a or 24b is released, causing the jaw 24a or 24b to close over the distal tissue flap 14 and lock it against the center plate 20. The other trigger 24a or 24b is then released, causing the other jaw 24a or 24b to close, engaging the tissue of the proximal flap 13 between the jaw 24a or 24b and the central plate 20. The application of the stapling and or suture is now easy and expeditious as shown in FIGS. 4a, b, and c which show the flaps 13 and 14a held together by the approximator 10 in FIG. 4a, the suturing partially complete in FIG. 4b and the completed job in FIG. 4c.

The problems with approximating the two flaps 13 and 14 are thereby eliminated. Presently, a stapler is used to staple a loose point A to a fixed point A in a cumbersome and time consuming sequence. It is not unusual for the loose point A of the proximal flap to be pushed away by the stapler before the staple is fired and miss it altogether or hold a minimal amount of tissue at point A of the proximal peritoneal flap 13.

Figure 6B:
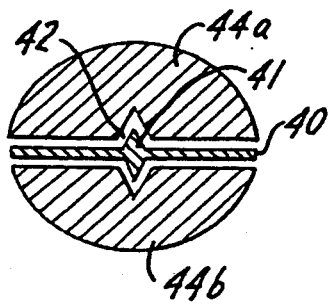
FIGS. 6a and b, shows schematically alternate embodiments of the jaws and central plate with FIG. 6a illustrated in the embodiment of FIG. 1.
Figure 6A:
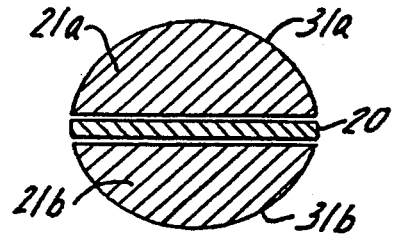
Figure 5:
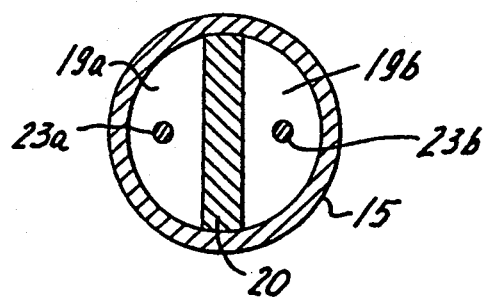
FIG. 5, shows a cross sectional view of the cylinder along the line 5—5 of FIG. 1.

FIG. 6b discloses and alternate embodiment to the invention wherein the central plate 40 has protruding teeth 41 on both sides and the jaws 44a, 44b have concave inner portions 42 to engage the teeth. This facilitates positive engagement with the flaps 13 and 14. FIG. 6a shows schematically the operation of the jaws 21a, 21b in the preferred embodiment.

While the above invention has been illustrated in conjunction with the drawings, it is possible that other embodiments utilizing the teachings of this invention may be devised and yet will fall within the spirit and scope of this invention. This invention covers all likely alternative embodiments.

What is claimed:

1. An apparatus for approximating tissue in laparoscopic surgery comprising:
    an elongated hollow cylinder having a handle at one end and a central plate extending along the cylinder and projecting outwardly from the other open end of the cylinder,
    a pair of triggers pivotally mounted to the cylinder adjacent to the handle,
    a separate control wire mounted within the cylinder to each trigger and extending along the cylinder, and
    a pair of jaws pivotally mounted adjacent the open end of the cylinder and each jaw mounted to the particular control wire to be operated thereby, said jaws pivoting into engagement with the plate when the corresponding trigger is operated to approximate tissue therebetween.

2. An apparatus in accordance with claim 1 wherein:
    each jaw comprises a member having a curved outer surface, a flat inner surface for engagement with the central plate for approximating tissue therebetween and an upwardly extending portion pivotally connected to the control wire for actuation.

3. An apparatus in accordance with claim 2 wherein:
    the cylinder comprises a first compartment and a second compartment separated by the central plate, each compartment having one of said control wires extending therealong from the trigger to the corresponding jaw.

4. An apparatus in accordance with claim 1 wherein the apparatus further includes:
    a pair of upper flange portions mounted on the cylinder having one of said triggers pivotally mounted to each flange portion, each trigger portions extending within the cylinder to engage a particular one of said control wires to effectuate movement.

5. An apparatus in accordance with claim 4 further including:
    resilient means mounted to each trigger at one end and to the handle at the other end to maintain each trigger in a fixed position.

6. An apparatus in accordance with claim 1 wherein:
    the jaws are each short, rigid and affixed to one of said control wires and wherein each control wire is substantially straight.

7. The method of approximating tissue in laparoscopic surgery wherein a proximal and distal flap are involved comprising the steps of:
    providing an approximator comprising a hollow cylinder having a pair of independently operable jaws extending outwardly at one end and a corresponding trigger for each jaw,
    providing a central plate extending along the cylinder and projecting outwardly from one end of the cylinder between the jaws,
    operating the trigger to close a first jaw against the central plate with the proximal tissue flap therebetween,
    moving the approximator with the proximal tissue held against the plate by one of the jaws to the vicinity of the distal flap,
    operating the other trigger to grasp the distal flap with the other jaw against the opposite side of the central plate, and,
    holding the tissue flaps in an adjacent relationship to facilitate suturing or stapling.

8. The method in accordance with claim 7 further including the step of:
    moving the approximator to a second position to approximate the proximal and distal flaps after the flaps that were initially approximated have been sutured.

9. The method in accordance with claim 8 wherein:
    the approximator is controlled with one hand operation of the triggers, each of said triggers being independently operable.

* * * * *